United States Patent [19]

Bundy

[11] 4,275,213

[45] Jun. 23, 1981

[54] ISOXAZOLYL DERIVATIVES OF 9α,11α-EPOXY IMINO-9,11,15-TRIDEOXY-PGF-TYPE COMPOUNDS

[75] Inventor: Gordon L. Bundy, Portage, Mich.

[73] Assignee: The Upjohn Company, Kalamazoo, Mich.

[21] Appl. No.: 148,631

[22] Filed: May 12, 1980

[51] Int. Cl.³ ................. C07D 261/04; C07D 413/12; C07D 413/06
[52] U.S. Cl. .................................. 548/240; 542/400; 542/413; 542/421; 542/426; 542/427; 542/435; 544/137; 546/209; 546/275
[58] Field of Search ................ 548/240; 546/275, 209; 544/137; 542/400, 413, 427, 421, 438, 426

[56] References Cited

U.S. PATENT DOCUMENTS 4,112,224   9/1978   Bundy ................................. 544/137

*Primary Examiner*—Arthur P. Demers
*Attorney, Agent, or Firm*—Lawrence T. Welch

[57] ABSTRACT

The present invention provides novel isoxazolyl derivatives prepared from 9α,11α-epoxyimino-9,11,15-trideoxy-PGF-type compounds. These novel compounds are useful as anti-inflammatory agents, anti-asthma agents, and platelet aggregation inhibitors in mammals and especially in humans.

45 Claims, No Drawings

ISOXAZOLYL DERIVATIVES OF 9α,11α-EPOXY IMINO-9,11,15-TRIDEOXY-PGF-TYPE COMPOUNDS

DESCRIPTION

1. Background of the Invention

The present invention provides novel compositions of matter. This invention further provides novel processes for preparing these compositions of matter. In particular this invention provides novel isoxazolyl derivatives prepared from 9α, 11α-epoxyimino-9,11,15-trideoxy PGF-type compounds. These novel compounds are useful for the same purposes as the known PGF-type compounds from which they are derived.

The term "PGF-type compounds" is used to describe certain structural and pharmacological analogs of the prostaglandins. The prostaglandins are a family of 20 carbon atom fatty acids, being structural derivatives of prostanoic acid, which exhibit useful activity in a wide variety of biological systems. Accordingly, such prostaglandins represent useful pharmacological agents in the treatment and prevention of a wide variety of disease conditions. For a fuller discussion of the prostaglandins, particularly PGF-type compounds, see Bergstrom, et al., Pharmacological Reviews 20:1 (1968), and references cited therein. For a discussion of the 9α,11α-epoxyimino-9,11,15-trideoxy-PGF-type compounds from which the compounds of this invention are derived, see U.S. Pat. No. 4,112,224.

2. Prior Art

9α,11α-Epoxyimino-9,11,15-trideoxy-PGF-type compounds are useful as anti-inflammatory agents, anti-asthma agents, and platelet aggregation inhibitors in mammals and especially in humans. They are described in U.S. Pat. No. 4,112,224.

SUMMARY OF THE INVENTION

The present invention provides a compound of the formula I, or a pharmacologically acceptable salt thereof wherein D represents the E or Z configuration.
wherein $M_1$ is oxo, α—OH:β—H, β—OH:α—H, α—OOH:β—H, or β—OOH:α—H;
wherein $X_1$ is
(1) —$CO_2R_1$, wherein $R_1$ is hydrogen, alkyl of from one to 12 carbon atoms, cycloalkyl of from 3 to 10 carbon atoms, aralkyl of from 7 to 12 carbon atoms, phenyl, phenyl mono-, di-, or trisubstituted by chloro or alkyl of from one to 3 carbon atoms, or phenyl para-substituted by
  (i) —NHCO—$R_{25}$
  (ii) —O—CO—$R_{26}$
  (iii) —$CO_2R_1$
  (iv) —O—CO—(p-Ph)—$R_{27}$
  (v) —CH=N—NH—CO—$NH_2$
wherein $R_{25}$ is methyl, phenyl, acetamidophenyl, benzamidophenyl, or amino, $R_{26}$ is methyl, amino or methoxy; $R_{27}$ is hydrogen or acetamido or a pharmacologically acceptable cation; and (p-Ph) is 1,4-phenylene,
(2) —$COW_1$, wherein $W_1$ is
  (a) amido of the formula-$NR_{21}R_{22}$, wherein $R_{21}$ and $R_{22}$ are:
    hydrogen;
    alkyl of one to 12 carbon atoms, inclusive;
    cycloalkyl of 3 to 10 carbon atoms, inclusive;
    aralkyl of 7 to 12 carbon atoms, inclusive;
    phenyl;
    phenyl substituted with one, 2, or 3 chloro, alkyl of one to 3 carbon atoms, inclusive, hydroxy, carboxy, alkoxycarbonyl of one to 4 carbon atoms, inclusive, or nitro;
    carboxyalkyl of one to four carbon atoms, inclusive;
    carbamoylalkyl of one to 4 carbon atoms, inclusive;
    cyanoalkyl of one to 4 carbon atoms, inclusive;
    acetylalkyl of one to 4 carbon atoms, inclusive;
    benzoylalkyl of one to 4 carbon atoms, inclusive;
    benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
    pyridyl;
    pyridyl substituted by one, 2, or 3 chloro, alkyl of one to 3 carbon atoms, inclusive, or alkoxy of one to 3 carbon atoms, inclusive;
    pyridylalkyl of one to 4 carbon atoms, inclusive; or
    pyridylalkyl substituted by one, 2, or 3 chloro, alkyl of one to 3 carbon atoms, inclusive, hydroxy, alkoxy of one to 3 carbon atoms, inclusive, hydroxyalkyl of one to 4 carbon atoms, inclusive, dihydroxyalkyl of one to 4 carbon atoms inclusive, or trihydroxyalkyl of one to 4 carbon atoms, inclusive;
    with the further proviso that not more than one of $R_{21}$ and $R_{22}$ is other than hydrogen or alkyl;
  (b) cycloamido selected from the group consisting of
    1-pyrrolidinyl,
    1-piperidinyl,
    4-morpholinyl,
    hexahydro-1H-azepin-1-yl,
    3-pyrrolin-1-yl, or
    3,6-dihydro-1(2H)-pyridinyl, substituted by $R_{21}$ or $R_{22}$ or both or
    1-piperazinyl substituted at the 4 position by $R_{21}$, wherein $R_{21}$ and $R_{22}$ are as defined above;
  (c) carbonylamido of the formula—$NR_{23}COR_{21}$, wherein $R_{23}$ is hydrogen or alkyl of one to 4 carbon atoms and $R_{21}$ is as defined above;
  (d) sulfonylamido of the formula—$NR_{23}SO_2R_{21}$, wherein $R_{21}$ and $R_{23}$ are as defined above; or
  (e) hydrazino of the formula—$NR_{23}R_{24}$, wherein $R_{24}$ is amido of the formula—$NR_{21}R_{22}$, as defined above, or cycloamido, as defined above; or
(3) $CH_2OH$
(4) —$CH_2NR_{11}R_{12}$ wherein $R_{11}$ and $R_{12}$ are the same or different and are hydrogen or alkyl of from one to 4 carbon atoms; wherein $Z_1$ is
  (1) cis—CH=CH—$CH_2(CH_2)_g$—$CH_2$—,
  (2) cis—CH=CH—$CH_2(CH_2)_g$—$CF_2$—,
  (3) cis—$CH_2$—CH=CH—$(CH_2)_g$—$CH_2$—,
  (4) $(CH_2)_3$—$(CH_2)_g$—$CH_2$—,
  (5) —$(CH_2)_3$—$(CH_2)_g$—$CF_2$—,
  (6) —$CH_2$—O—$CH_2$—$(CH_2)_g$—$CH_2$—,
  (7) —(m—Ph)—$CH_2(CH_2)_g$—, or
  (8) —(m-Ph)—O—$(CH_2)_g$—, wherein (m-Ph) is 1,3-phenylene and g is an integer from one to 3;
wherein $L_1$ is α-$R_3$:β-$R_4$, β-$R_3$:α-$R_4$ or a mixture of the two, wherein $R_3$ and $R_4$ are the same or different and are hydrogen, methyl, or fluoro, with the provision that if $R_3$ is fluoro, $R_4$ is hydrogen or fluoro;
wherein $R_7$ is
  (1) —$(CH_2)_m$—$CH_3$
  (2) —O—(PhI)
  (3) —$(CH_2)_n$—(PhI)

wherein m is an integer from one to 5, n is an integer from 0 to 4, and (PhI) is phenyl substituted by from 0 to 3, chloro, fluoro, trifluoromethyl, alkyl of from one to 3 carbon atoms, or alkoxy of from one to 3 carbon atoms, with the proviso that not more than two substituents are other than alkyl.

Examples of phenyl esters substituted in the para position (i.e., $X_1$ is —$COOR_1$, $R_1$ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylamidophenyl ester, p-acetylphenyl ester, p-benzylphenyl ester, p-amidocarbonylphenyl ester, p-methoxycarbonylphenyl ester, p-benzoyloxyphenyl ester, p-(p-acetamidobenzoyloxy)phenyl ester and p-hydroxybenzaldehyde semicarbazone ester.

Examples of novel amides herein (i.e., $X_1$ is $COL_4$) include the following:

(1) Amides within the scope of alkylamido groups of the formula —$NR_{21}R_{22}$ are methylamide, ethylamide, n-propylamide, n-butylamide, n-pentylamide, n-hexylamide, n-heptylamide, n-octylamide, n-nonylamide, n-decylamide, n-undecylamide, and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide and propylbutylamide. Amides within the scope of cycloalkylamido are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, N-ethyl-N-cyclohexylamide, dicyclopentylamide, and dicyclohexylamide. Amides within the scope of aralkylamido are benzylamide, 2-phenylethylamide, N-methyl-N-benzylamide, and dibenzylamide. Amides within the scope of substituted phenylamido are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methylanilide, p-ethylanilide, t-butylanilide, p-carboxyanilide, p-methoxycarbonylanilide, o-carboxyanilide and o-hydroxyanilide. Amides within the scope of carboxyalkylamido are carboxyalkylamido, carboxymethylamide, carboxyethylamide, carboxypropylamide, and carboxybutylamide. Amides within the scope of the carbamoylalkylamido are carbamoylmethylamide, carbamoylethylamide, carbomoylpropylamide, and carbamoylbutylamide. Amides within the scope of cyanoalkylamido are cyanomethylamide, cyanoethylamide, cyanopropylamide and cyanobutylamide. Amides within the scope of acetylalkylamido are acetylmethylamide, acetylethylamide, acetylpropylamide, and acetylbutylamide. Amides within the scope of benzoylalkylamido are benzoylmethylamide, benzoylethylamide, benzoylpropylamide, and benzoylbutylamide. Amides within the scope of substituted benzoylalkylamido are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethylbenzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butyl benzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5-trimethoxybenzoylethylamide, p-hydroxymethylbenzoylethylamide, p-methylbenzoylethylamide, m-methylbenzoylethylamide, p-ethylbenzoylethylamide, t-butyl-benzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutylamide, m-methylbenzoylbutylamide, p-ethylbenzoylbutylamide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamido are α-pyridylamide, β-pyridylamide, and γ-pyridylamide. Amides within the scope of substituted pyridylamido are 4-methyl-α-pyridylamide, 4-methyl-β-pyridylamide, 4-chloro-α-pyridylamide, and 4-chloro-β-pyridylamide. Amides within the scope of pyridylalkylamido are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamido are 4-methyl-α-pyridylmethylamide, 4-methyl-β-pyridylmethylamide, 4-chloropyridylmethylamide, 4-chloro-β-pyridylmethylamide, 4-methyl-α-pyridylethylamide, 4-methyl-β-pyridylethylamide, 4-chloropyridylethylamide, 4-chloro-β-pyridylethylamide, 4-methyl-α-pyridylpropylamide, 4-methyl-β-pyridylpropylamide, 4-chloro-pyridylpropylamide, 4-chloro-β-pyridylpropylamide, 4-methyl-β-pyridylbutylamide, 4-methyl-α-pyridylbutylamide, 4-chloropyridylbutylamide, 4-chloro-β-pyridylbutylamide, 4-methyl-β-pyridylbutylamide. Amides within the scope of hydroxyalkylamide are hydroxymethylamide, α-hydroxyethylamide, β-hydroxyethylamide, α-hydroxypropylamide, β-hydroxypropylamide, γ-hydroxypropylamide, 1-(hydroxymethyl)-ethylamide, 1-(hydroxymethyl)propylamide, (2-hydroxymethyl)propylamide, and α,α-dimethyl-β-hydroxy ethylamide. Amides within the scope of dihydroxyalkylamide are dihydroxymethylamide, α,α-dihydroxyethylamide, α,β-dihydroxyethylamide, β,β-dihydroxyethylamide, α,α-dihydroxypropylamide, α,β-dihydroxypropylamide, α,γ-dihydroxypropylamide, β,β-dihydroxypropylamide, β,γ-dihydroxypropylamide, γ,γ-dihydroxypropylamide, 1-(hydroxymethyl)-2-hydroxyethylamide, 1-(hydroxymethyl)-1-hydroxyethylamide, α,α-dihydroxybutylamide, α,β-dihydroxybutylamide, α,γ-dihydroxybutylamide, α,δ-dihydroxybutylamide, α,δ-dihydroxybutylamide, β,β-dihydroxbutylamide, β,γ-dihydroxybutylamide, γ,δ-dihydroxybutylamide, γ,γ-dihydroxybutylamide, γ,δ-dihydroxydroxybutylamide, δ,δ-dihydroxybutylamide, and 1,1-bis(hydroxymethyl)ethylamide. Amides within the scope of trihydroxyalkylamino are tris(hydroxymethyl)methylamide and 1,3-dihydroxy-2-hydroxymethyl-propylamide.

(2) Amides within the scope of the cycloamido groups described above are pyrrolidylamide, piperidylamide, morpholinylamide, hexamethyleneiminylamide, piperazinylamide, pyrrolinylamide, and 3,4-didehydropiperidinylamide.

(3) Amides within the scope of carbonylamido of the formula $-NR_{23}COR_{21}$ are methylcarbonylamide, ethylcarbonylamide, phenylcarbonylamide, and benzylcarbonylamide. Amides within the scope of sulfonylamido of the formula $-NR_{21}SO_2R_{21}$ are methylsulfonylamide, ethylsulfonylamide, phenylsulfonylamide, p-tolylsulfonylamide, benzylsulfonylamide, (4) Hydrazines within the scope of the above hydrazino groups are hydrazine, N-aminopiperidine, benzoylhydrazine, N-aminomorpholine, 2-hydroxyethylhydrazine, methylhydrazine, 2,2,2-hydroxyethylhydrazine and p-carboxyphenylhydrazine.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of -(PhI) are phenyl, (o-, m-, or p-)tolyl, (o-, m-, or p-)ethylphenyl, 2-ethyl-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-,4-,5- or 6-(chloro-o-tolyl, 4-chloro-2-propylphenyl, 2-isopropyl-4-chlorophenyl, 4-chloro-3,5-xylyl, (2,3- 2,4- 2,5- 2,6- or 3,5-)dichlorophenyl, 4-chloro-3-fluorophenyl, (3- or 4-)chloro-2-fluorophenyl, (o-, m-, or p-)trifluoro-methylphenyl), (o-, m-, or p-)ethoxyphenyl, (4- or 5-)chloro-2-methoxy-phenyl, and 2,4-dichloro-(5- or 6-)methylphenyl.

With regard to the divalent substituents described above(e.g., $L_1$ and $M_1$), these divalent radicals are defined as $\alpha\text{-}R_i{:}\beta\text{-}R_j$, wherein $R_i$ represents the substituent of the divalent moiety in the alpha configuration with respect to the ring and $R_j$ represents the substituent of the divalent moiety in the beta configuration with respect to the plane of the ring. Accordingly, when $M_1$ is defined as $\beta\text{-}OH{:}\beta\text{-}H$, the hydroxy of the $M_1$ moiety is in the alpha configuration, and the hydrogen substituent is in the beta configuration.

While the compounds of the present invention are derivatives of prostaglandin analogs, they will be named herein as analogs of long chain fatty acids, using the Chemical Abstracts numbering system (see Naming and Indexing of Chemical Substances for Chemical Abstracts during the Ninth Collective Period (1972–1976), a reprint of section IV from the Volume 76 Index Guide). A heptadecadienoic acid will be formed whenever a prostaglandin analog of 20 carbon chain length is used as the starting material. See U.S. Pat. No. 4,112,224 for a discussion of the parent compounds and their nomenclature.

When $M_1$ is hydroxy or hydroperoxy, there are four possible isomeric configurations of the combination of the bond D and the sterochemistry of the hydroxy or hydroperoxy substituent. These are depicted as the Formula XX–XXIII isomers in Chart B. These isomers are of varying polarity. Each of the four isomers is converted to one of the two configurations of the compounds of formula I wherein $M_1$ is oxo. Refer to Formula XIII prepared by step 3 of Chart A. The two possible configurations of the compounds of formula XIII are depicted as Formulas XXV and XXVI of Chart C.

When a 20 carbon prostaglandin analog is used as the Formula X starting material, a Formula XI heptadecanoic acid is formed. The two possible isomers occur at the number 11 carbon on that structure. For convenience, the two possible C-11 isomers for each of the 9Z and 9E isomers will be referred to as either the "more polar C-11 epimer" or the "less polar C-11 epimer." Any given heptadecanoic acid wherein $M_1$ is hydroxy or hydroperoxy will thus have a 9Z more polar C-11 epimer, a 9Z less polar C-11 epimer, a 9E more polar C-11 epimer and a 9E less polar C-11 epimer. The Greek symbol "ξ" indicates the two possible configurations at the designated carbon e.g. "11ξ."

An advantage of the claimed compounds over the prior art compounds from which they are derived is their increased selectivity for platelet aggregation with less pronounced other effects normally associated with the prostaglandin compounds (e.g., smooth muscle stimulation, reduction in blood pressure and the like). The compounds of the present invention are thus surprisingly and unexpectedly improved pharmacological agents, being more selective and more stable than the prior art compounds.

The novel compounds of this invention are highly active as inhibitors of the thromboxane synthetase enzyme system. Accordingly, these novel compounds are useful for administration to mammals, including humans, whenever it is desirable medically to inhibit this enzyme system. For example, these novel compounds are useful as anti-inflammatory agents in mammals and especially humans, and for this purpose, are administered systemically and preferably orally. For oral administration, a dose range of 0.05 to 50 mg per kg of human body weight is used to give relief from pain associated with inflammatory disorders such as rheumatoid arthritis. They are also administered intravenously in aggravated cases of inflammation, preferably in a dose range 0.01 to 100 µg per kg per min until relief from pain is attained. When used for these purposes, these novel compounds cause fewer and lesser undesirable side effects than do the known synthetase inhibitors used to treat inflammation, for example, aspirin and indomethacin. When these novel compounds are administered orally, they are formulated as tablets, capsules, or as liquid preparations, with the usual pharmaceutical carriers, binders, and the like. For intravenous use, sterile isotonic solutions are preferred.

The novel compounds of this invention are useful in the treatment of asthma, for example, as bronchodilators or as inhibitors of mediators, such as SRS-A and histamine which are released from cells activated by an antigen-antibody complex. Thus, these compounds control spasm and facilitate breathing in conditions such as bronchial asthma, bronchitis, bronchiectasis, pneumonia, and emphysema. For these purposes, the compounds are administered in a variety of dosage forms, e.g., orally in the form of tablets, capsules, or liquids; rectally in the form of suppositories; parenterally; subcutaneously; or intramuscularly; with intravenous administration being preferred in emergency situations; by inhalation in the form of aerosols or solutions for nebulizers; or by insufflation in the form of powder. Doses in the range of about 0.01 to 50 mg per kg of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, epinephrine, etc.); xanthine derivatives (theophylline and aminophylline); and corticosteroids (ACTH and prednisolone. Regarding use of these compounds see M. E. Rosenthale, et al., U.S. Pat. No. 3,644,638.

The novel compounds of this invention are useful in mammals, including humans, as nasal decongestants and are used for this purpose, in a dose range of about 10 µg. to about 10 mg per ml of a pharmacologically suitable liquid vehicle or as an aerosol spray, both for topical application.

These novel compounds are useful whenever it is desired to inhibit platelet aggregation, reduce the adhesive character of platelets, and remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclorosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid resonance especially in emergency situations, the intravenous route of administration is preferred. Doses in the range about 0.005 to about 20 mg per kg of body weight per day are used, the exact dose depending on the age, weight, and condition of the patient or animal, and on the frequency and route of administration.

These novel compounds are further useful as additives to blood, blood products, blood substitutes, or other fluids which are used in artificial extracorporeal circulation or perfusion of isolated body portions, e.g., limbs and organs, whether attached to the original body, detached and being preserved or prepared for transplant, or attached to a new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg per liter of circulating fluid. It is especially useful to use these compounds in laboratory animals, e.g., cats, dogs, rabbits, monkeys, and rats, for these purposes in order to develop new methods and techniques for organ and limb transplants.

When $X_1$ is $-COOR_1$, the novel compounds are used for the purposes described above in the free acid form, in ester form, and in the pharmacologically acceptable salt form. When the ester form is used, the ester is any of those within the above definition of $R_1$. However, it is preferred that the ester be alkyl of one to 12 carbon atoms, inclusive. Of the alkyl esters, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of the novel compounds of this invention useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine catins are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and the like aliphatic, cycloaliphatic, araliphatic amines containing up to and including about 18 carbon atoms, as well as heterocyclic amines, e.g., piperidiene, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amine containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, glactamine, N-methylglycamine, N-methylglucosamine, ephedrine, phenylephrine, epinephrine, procaine, and the like. Further useful amine salts are the basic amino acid salts, e.g., lysine and arginine.

Examples of suitable pharmacologically acceptable quaternary ammonium cations are tetramethylammonium, tetraethylammonium, benzyltrimethylammonium, phenyltriethylammonium, and the like.

Certain compounds of the present invention are preferred to obtain the optimal combination of biological response, specificity, potency, and duration of activity. Thus, compounds of the formula I, wherein $X_1$ is —$CO_2H$ or —$CO_2CH_3$, $Z_1$ is —CH=CH—$CH_2CH_2CH_2$—, $R_3$ and $R_4$ are hydrogen, and $R_7$ is —$(CH_2)_3CH_3$ are preferred. Compounds which satisfy one or more of these preferences are preferred and compounds satisfying all of these preferences are most preferred.

The compounds of the present invention are formed by thermal-oxidation of a 9α,11α-epoxyimino-9,11-15-trideoxy-PGF-type compound of the formula X wherein all variables are defined as above. This is illustrated in Chart A. This oxidative decomposition of compounds of the formula X into the isoxazoline hydroperoxide of the formula XI occurs in the absence of solvents or in the presence of ethyl acetate, ethanol, tetrahydrofuran, or similar inert organic solvents. The rate of the reaction is substantially independent of the nature of the solvent or the presence of mild acids. The reaction occurs equally well in the light or in the dark. The only critical element is that the reactants be exposed to air, i.e., oxygen.

A preferred means to prepare the compounds of the present invention is to reflux a compound of the formula X in an easily removable solvent such as ethyl acetate. The rate of reaction is greatly increased by the application of heat. While the temperature of the reaction is not critical, it should be high enough to allow the reaction to proceed at a reasonable rate, but not so high as to cause destruction of the reactant or final product. Essentially, no reaction occurs at −20° C. It is very slow at 25° C., and it is fairly rapid at 50° C. A preferred temperature range for the reaction is from 30° to 80° C.

Hydroperoxide compounds of the formula XI are converted to alcohol compounds of the formula XII using conventional methods such as zinc in acetic acid or sodium borohydride in methanol. Conversion of hydroxy compounds of the formula XII to the corresponding ketone of the formula XIII is accomplished by reacting a compound of formula XIi with an oxidizing agent.

The oxidizing agents that are used include: Jones Reagent (acidified chromic acid, see Journal of American Chemical Society, 39 (1946)), Collins Reagent (chromium trioxide in pyridine, see Collins, et al., Tetradedron Lett., 3363 (1968)), mixtures of chromium trioxide in pyridine, see Journal of the American Chemical Society 75, 422 (1953)), tert-butyl chromate in pyridine (see Biological Chemistry Journal, 84, 195 (1962)), mixtures of sulfur trioxide in pyridine and dimethyl sulfoxide (see Journal of the American Chemical Society, 89, 5505 (1967)), and mixtures of dicyclohexylcarbodiimide and dimethylsulfoxide (see Journal of the American Chemical Society, 87, 5661 (1965)).

When $X_1$ is an alkyl ester such as methyl ester, the corresponding acid may be obtained by enzymatic hydrolysis using Plexaura homomalla-derived esterase. For a description of this process see W. P. Schneider, et al., J. Am. Chem. Soc. 99, 1222 (1977). This is depicted in Chart D.

DESCRIPTION OF THE PREFERRED EMBODIMENTS

The present invention is more fully understood by the examples set out below.

EXAMPLE 1

Preparation of (5Z,8R,9Z,11ξ) and (5Z,8R,9E,11ξ)-8-(4,5-dihydro-5-isoxazolyl)-11-hydroperoxy-5,9-heptadecadienoic acid, methyl esters. (Formula I, $X_1$ is —$CO_2CH_3$, $Z_1$ is cis—CH=CH—$(CH_2)_3$—, $M_1$ is α-OOH:β-H or α-H:β-OOH, $R_3$ and $R_4$ are hydrogen, $R_7$ is —$(CH_2)_3$—$CH_3$, D is cis or trans)

Refer to Chart A, step 1.

A solution containing 9.0 g of purified 9α,11α-(epoxyimino)-prosta-5Z,13E-dien-1-oic acid, methyl ester in 900 ml of ethyl acetate is placed in a 2 l round bottom flask, stoppered, and allowed to stand at 22°±2° C. for 6 weeks. The atmosphere in the flask is air. TLC analysis, using 40% ethyl acetate/hexane, shows that the starting material has been completely coverted to 4 less polar compounds. Following removal of the solvent in vacuo, the residue is chromatographed on a column containing 1.6 kg of 40-60μ silica gel. The column is packed dry, equilibrated with 20% ethyl acetate/hexane, and eluted with 12 l of the same solvent. This solvent is then discarded. The column is then eluted with 16 l of 30% ethyl acetate/hexane in 50 ml fractions, and finally eluted with 10 l of 35% ethyl acetate/hexanes.

The fractions are combined as follows based on their Rf values using TLC with a 40% ethyl acetate/hexane solvent. Fractions 14-40: contain 852 mg of the less polar 9-cis compound, fractions 66-90 contain 1.81 g of the less polar 9-trans compound, fractions 186-225 contain 1.47 g of the more polar 9-cis compound, fractions 226-245 contain 707 mg of a mixture of the more polar 9-cis and more polar 9-trans compound, and fractions 246-305 contain 1.27 gm of the more polar 9-trans compound. These compounds are characterized as follows:

The less polar 9Z isomer has IR peaks at 3380, 3000, 1730, 1600, 850, and 800 $cm^{-1}$. The NMR peaks ($CHCl_3$, δ) observed are at δ 8.7 (broad m, 1H shifts downfield on cooling) 7.15-7.04 (m, 1H), 5.7-5.3 (m, 4H), 4.80-4.25 (m, 2H), 3.66 (S, 3H), and 3.05-2.65 ppm (m, 2H). The mass spectrum shows ions observed at 381 (M +), 364, 348, 316, 278, 206, 165, and 113. The C:H:N ratio is 65.35:10.54:3.80.

For the less polar 9E isomer, the characterization data is as follows:

The infrared spectrum shows peaks observed at 3400, 3000, 1730, 1600, 970, shows 845 $cm^{-1}$. The NMR spectrum and $CDCl_3$ and TMS peaks observed at δ 8.4 (broad m, 1H, shifts downfield on cooling), 7.17-6.95 (m, 1H), 5.65-5.25 (m, 4H), 4.85-4.05 (m, 2H), 3.66 (s, 3H) and 3.10-2.65 ppm (m, 2H). The mass spectrum shows ions observed at M/E of 381 (m+), 364, 348, 316, 278, 223, 206, and 165. The C:H:N ratio is 65.60:9.48:3.83.

The more polar 9Z isomer has characterization data as follows:

The IR spectrumshows peaks observed at 3380, 3000, 1730, 1600, 1020, 845, and 800 cm$^{-1}$. The NMR spectrum (CDCl$_3$, δ) peaks observed are 8.63 (broad m, 1H, shifts downfield on cooling), 7.15–7.00 (m, 1H), 5.65–5.20 (m, 4H), 4.85–4.35 (m, 2H), 3.66 (s, 3H), and 3.10–2.80 ppm (m, 2H). The mass spectrum shows ions observed at M/E of 381 (m+), 364, 349, 348, 316, 278, 165, 113. The C:H:N ratio is 65.70:9.27:3.66.

The more polar 9E isomer is characterized as follows:

The infrared spectrum shows peaks observed at 3400, 3000, 1730, 1600, 970, and 845 cm$^{-1}$. The NMR (CDCl$_3$, δ) peaks observed are as follows:

8.44 (m, 1H, shifts downfield on cooling), 7.10–7.00 (m, 1H), 5.60–5.25 (m, 4H), 4.85–4.05 (m, 2H), 3.66 (s, 3H) and 3.10–2.75 ppm (m, 2H). The mass spectrum shows ions observed at M/E of 381 (M+), 364, 349, 348, 278, 223, 206, 165.

Alternatively, these compounds are prepared by dissolving 5 mg of 9α,11α-(epoxyimino)-prosta-5Z,13E-dien-1-oic acid, methyl ester in 1 ml of ethyl acetate. The mixture is heated to 50° C. in an oxygen atmosphere. The reaction is complete in about 22 hr.

EXAMPLE 2

(5Z,8R,9Z,11ξ)-8-(4,5-dihydro-5-isoxazolyl)-11-hydroxy-5,9-heptadecadienoic acid methyl ester. (Less Polar C-11 Epimer) (Formula I, X$_1$ is —CO$_2$CH$_3$, Z$_1$ is cis—CH=CH—(CH$_2$)$_3$, M$_1$ is α-OH:β-H, R$_3$ and R$_4$ are hydrogen, R$_7$ is —(CH$_2$)$_3$—CH$_3$, D is cis)

Refer to Chart A, step 2.

A solution of 75 mg of (5Z,8R,9Z,11ξ)-8-(4,5-dihydro-5-isoxazolyl)-11-hydroperoxy-5,9-heptadecadienoic acid methyl ester having the less polar of the two configurations at C-11 is dissolved in 3 ml of acetic acid and is treated with 50 mg of zinc dust, and the resulting gray suspension is stirred for 3 hours at 25° C. The reaction mixture is then poured into a mixture of ice, brine, and aqueous sodium bicarbonate and extracted with ethyl acetate. The extracts are washed with brine, dried over anhydrous magnesium sulfate and concentrated. The crude product is chromatographed on a column containing 20 g of silica gel. The column is packed with 20% ethyl acetate/hexane and eluted with 200 ml of 30% ethyl acetate/hexane. The product was eluted in 3 ml fractions. Fractions 35–48 are combined based on their similar Rf values to yield 65 mg of pure title product as a viscous, colorless oil. The ferrous thiocyanate spray test for peroxides is negative, indicating all of the hydroperoxide is converted to the hydroxide.

IR absorptions are observed at 3440, 3000, 1730, 1600, 1360, 1160, 1030, 1010, 850 and 800 cm$^{-1}$. NMR absorptions (CDCl$_3$, δ) are observed at 7.15–7.05 (m, 1H), 5.85–5.05 (M, 4H), 4.85–4.05 (m, 2H), 3.66 (S, 3H), 3.05–2.60 (m-2H) and 1.80 ppm (broad singlet, 1H, shifts downfield on cooling).

EXAMPLE 3

(5Z,8R,9E,11ξ)-8-(4,5-dihydro-5-isoxazolyl)-11-hydroxy-5,9-heptadienoic acid methyl ester (Less polar C-11 epimer) (Formula I, X$_1$ is —CO$_2$CH$_3$, Z$_1$ is cis—CH=CH—(CH$_2$)$_3$, M$_1$ is α-OH:β-H, R$_3$ and R$_4$ are hydrogen, R$_7$ is —(CH$_2$)$_3$—CH$_3$, D is trans)

Refer to Chart A, step 2.

A solution of 80 mg of (5Z,8R,9E,11ξ)-8-(4,5-dihydro-5-isoxazolyl)-11-hydroperoxy-5,9-heptadienoic acid methyl ester having the less polar of the two configurations at C-11 is dissolved in 10 ml of methanol and is cooled at 0° C. and treated with 15 mg of sodium borohydride. The reaction mixture is stirred for 15 min at 0° C., for 1 hr at 25° C. and then poured into ice and brine containing a small amount of citric acid and extracted with 1:1 ethyl acetate/hexane solution having a pH in the aqueous layer of 7.5. The organic layer is washed with brine, dried over anhydrous magnesium sulfate and concentrated. The crude product (79 mg) is chromatographed on 18 gm of silica gel. The column is packed with 25% ethyl acetate/hexane and eluted with 100 ml of 35% ethyl acetate/hexane followed by 100 ml of 40% and 100 ml of 50% ethyl acetate/hexane. The eluant is recovered in 3 ml fractions. Fractions 45–59 are combined based on similar Rf values, yielding 40 mg of pure titled product as a viscous, colorless oil. The ferrous thiocyanate peroxide test was negative, indicating all of the hydroperoxide is converted to the hydroxide.

IR absorptions are observed at 3450, 3000, 1735, 1600, 1360, 1030, 980 and 850 cm$^{-1}$. NMR absorptions (CDCl$_3$, δ) are observed at δ 7.08–6.95 (M, 1H), 5.70–5.15 (M, 4H), 4.85–4.30 (M, 1H), 4.25–3.85 (M, 1H), 3.66 (S, 3H), 3.05–2.65 (M, 2H), and 1.85 ppm (S, 1H, shifts downfield on cooling).

EXAMPLE 4

(5Z,8R,9Z,11ξ)-8-(4,5-dihydro-5-isoxazolyl)-11-hydroxy-5,9-heptadecadienoic acid methyl ester (more polar C-11 epimer) (Formula I, X$_1$ is —CO$_2$CH$_3$, Z$_1$ is cis—CH=CH—(CH$_2$)$_3$, M$_1$ is α-OH:β-H, R$_3$ and R$_4$ are hydrogen, R$_7$ is —(CH$_2$)$_3$—CH$_3$, D is cis)

Following the procedure given in Example 2, 30 mg of the hydroperoxide corresponding to more polar C-11 configuration of the titled product is reduced with 15 mg of zinc dust and 1 ml of acetic acid. The crude product, 32 mg, is chromatographed on a column containing 20 g of silica gel. The column is packed with 30% ethyl acetate/hexane and eluted in 3 ml fractions with 100 ml of 50% and 100 ml of 65% ethyl acetate/hexane. Fractions 44–52 were combined based on similar TLC and yield 22 mg of pure titled product as a viscous, colorless oil. The ferrous thiocyanate spray test for peroxides is negative, indicating all of the hydroperoxide is converted to the hydroxide.

IR absorptions are observed at 3440, 3000, 1730, 1600, 1150, 1040, 1000, 845 and 800 CM$^{-1}$. NMR absorptions (CDCl$_3$, δ) are observed at δ 7.15–7.05 (M, 1H), 5.80–5.10 (M, 4H), 4.75–4.05 (M, 2H), 3.66 (S, 3H), and 3.10–2.75 ppm (M, 2H).

EXAMPLE 5

(5Z,8R,9E,11ξ)-8-(4,5-dihydro-5-isoxazolyl)-11-hydroxy-5,9-heptadecadienoic acid methyl ester (more polar C-11 epimer) (Formula I, X$_1$ is —CO$_2$CH$_3$, Z$_1$ is cis—CH=CH—(CH$_2$)$_3$, M$_1$ is α-OH:β-H, R$_3$ and R$_4$ are hydrogen, R$_7$ is —(CH$_2$)$_3$—CH$_3$, D is trans)

Following the procedure given in Example 2, 60 mg of the hydroperoxide corresponding to the more polar C-11 configuration of the title product is reduced using 30 mg of zinc dust and 2 ml of acetic acid. The crude product is chromatographed on a column containing 20 g of silica gel. The column is packed with 40% ethyl acetate/hexane and eluted with 100 ml of 50% ethyl acetate/hexane. This is followed by 100 ml of 65% ethyl acetate/hexane and which is collected in 3 ml fractions. Fractions 33–46 are combined based on their similar Rf values and yield 50 mg of pure title product as a viscous, colorless oil. The ferrous thiocyanate peroxide test is negative.

IR absorptions are observed at 3440, 3000, 1735, 1600, 1160, 1030, 1000, 980 and 850 cm$^{-1}$. NMR absorptions (CDCl$_3$, δ) are observed at δ 7.10–7.00 (M, 1H), 5.60–5.25 (M, 4H), 4.85–4.35 (M, 1H), 4.25–3.85 (M, 1H), 3.66 (S, 3H), 3.05–2.70 (M, 2H) and 1.90 ppm (S, 1H, shifts downfield on cooling).

EXAMPLE 6

(5Z,8R,9Z,11ξ)-8-(4,5-dihydro-5-isoxazolyl)-11-hydroxy-5,9-heptadecadienoic acid (less polar C-11 epimer) (Formula I, $X_1$ is —COOH, $Z_1$ is cis—CH=CH—(CH$_2$)$_3$, $M_1$ is α-OH:β-H, $R_3$ and $R_4$ are hydrogen, $R_7$ is —(CH$_2$)$_3$—CH$_3$, D is cis)

Refer to Chart A, step 2.

A mixture of 130 mg of the less polar (5Z,8R,9Z,11ξ)-8-(4,5-dihydro-5-isooxazolyl)-11-hydroperoxy-5,9-heptadecadienoic acid C-11 epimer and 85 mg of zinc dust in 5 ml of acetic acid is stirred at 25° C. for 2.5 hr, then poured into brine and extracted with a 60/40 mixture of ethyl acetate/hexane. The extracts are washed three times with brine, dried over anhydrous magnesium sulfate and concentrated in vacuo. The crude product is chromatographed on a column containing 20 g of silica gel. The column is packed with 20% ethyl acetate/hexane containing 0.5% acetic acid and eluted in 3 ml fractions with 40% ethyl acetate/hexane containing 0.5% acetic acid. Fractions 41–65 are combined based on similar Rf values yielding 110 mg of pure title product as a viscous, colorless oil. The ferrous thiocyanates spray test is negative.

IR absorptions are observed at 3390, 3200, 3000, 2650, 1705, 1600, 1280, 1230, 850, 800 and 780 cm$^{-1}$. NMR absorptions (CDCl$_3$, δ) are observed at δ 7.15–7.04 (M, 1H), 6.55 (S, 2H shifts downfield on cooling), 5.80–5.05 (M, 4H), 4.80–4.05 (M, 2H) and 3.05–2.60 ppm (M, 2H).

EXAMPLE 7

(5Z,8R,9E,11ξ)-8-(4,5-dihydro-isoxazolyl)-11-hydroxy-5,9-heptadecadienoic acid (less polar C-11 epimer) (Formula I, $X_1$ is —COOH, $Z_1$ is cis—CH=CH—(CH$_2$)$_3$, $M_1$ is α-OH:β-H, $R_3$ and $R_4$ are hydrogen, $R_7$ is —(CH$_2$)$_3$—CH$_3$, D is trans)

Following the procedure of Example 6, 160 mg of the less polar C-11 epimer of the hydroperoxide corresponding to the title product is reduced using 105 mg of zinc dust in 6 ml of acetic acid. The crude product is chromatographed on 20 g of silica gel. The column is packed with 25% ethyl acetate/hexane containing 0.5% acetic acid and is eluted with 40% ethyl acetate/hexane in 2-4 ml fractions. Fractions 80–130 are combined based on similar Rf values and yield 105 mg of pure title product as a viscous, colorless oil with a negative ferrous thiocyanate test.

IR absorptions are observed at 3390, 3000, 2650, 1705, 1600, 1280, 1240, 975 and 850 cm$^{-1}$. NMR absorptions (CDCl$_3$, δ) are observed at δ 7.15–7.00 (M, 1H), 6.05 (S, 2H, shifts downfield on cooling), 5.70–5.25 (M, 4H), 4.85–4.35 (M, 1H), 4.25–3.90 (M, 1H), and 3.05–2.65 ppm (M, 2H).

EXAMPLE 8

(5Z,8R,9Z,11ξ)-8-(4,5-dihydro-5-isoxazolyl)-11-hydroxy-5-,9-heptadecadienoic acid (more polar C-11 epimer) (Formula I, $X_1$ is —COOH, $Z_1$ is cis—CH=CH—(CH$_2$)$_3$, $M_1$ is α-OH:β-H, $R_3$ and $R_4$ are hydrogen, $R_7$ is —(CH$_2$)$_3$—CH$_3$, D is cis)

Following the procedure described in Example 6, 150 mg of the more polar C-11 epimer of the hydroperoxide corresponding to the titled product is reduced with 100 mg of zinc dust in 5 ml of acetic acid. The crude product is chromatographed on a 20 g column of silica gel, packed with 40% ethyl acetate/hexane containing 0.5% acetic acid and eluted in 3 ml fractions with 100 ml of 50% ethyl acetate/hexanes in 100 ml of 60% ethyl acetate/hexane, and 100 ml of 70% ethyl acetate/hexanes, all containing 0.5% acetic acid. Fractions 53–90 were combined based on similar Rf values and yield 129 mg of pure title product as a viscous, colorless oil with a negative ferrous thiocyanate test.

IR absorptions are observed at 3350, 3000, 2650, 1705, 1600, 1040, 1000, 850 and 800 cm$^{-1}$. NMR absorptions (CDCl$_3$, δ) are observed at δ 7.22–7.07 (M, 1H), 6.50 (S, 2H, shifts downfield on cooling), 5.85–5.05 (M, 4H), 4.75–4.05 (M, 2H), and 3.1–2.75 ppm (M, 2H).

EXAMPLE 9

(5Z,8R,9E,11ξ)-8-(4,5-dihydro-5-isoxazolyl)-11-hydroxy-5,9-heptadecadienoic acid (more polar C-11 epimer) (Formula I, $X_1$ is —COOH, $Z_1$ is cis—CH=CH—(CH$_2$)$_3$, $M_1$ is α-OH:β-H, $R_3$ and $R_4$ are hydrogen, $R_7$ is —(CH$_2$)$_3$—CH$_3$, D is trans)

Following the procedure given in Example 6, 150 mg of the hydroperoxide corresponding to the title product is reduced using polar C-11 epimer of the 100 mg of zinc dust in 5 ml of acetic acid. The crude product is chromatographed on 20 g of silica gel. The column is packed with 50% ethyl acetate/hexane containing 0.5% acetic acid. The product is eluted in 3 ml fractions with 70% ethyl acetate/hexane containing 0.5% acetic acid. Fractions 46–75 are combined based on similar Rf values and yield 122 mg of pure title product as a colorless, viscous oil.

IR absorptions are observed at 3400, 3280, 3000, 2650, 1710, 1605, 1280, 1240, 980 and 850 cm$^{-1}$. NMR absorptions (CDCl$_3$, δ) are observed at δ 7.18–7.03 (M, 1H), 6.30 (S, 2H, shifts downfield on cooling), 5.65–5.15 (M, 4H), 4.85–4.35 (M, 1H), 4.25–3.90 (M, 1H), and 3.10–2.70 ppm (M, 2H).

EXAMPLE 10

(5Z,9Z)-8-(4,5-dihydro-5-isoxazolyl)-11-oxo-5,9-heptadecadienoic acid, methyl ester (Formula I, $X_1$ is —CO$_2$—CH$_3$, $Z_1$ is cis—CH=CH—(CH$_2$)$_3$—CH$_3$, $M_1$ is oxo, $R_3$ and $R_4$ are hydrogen, $R_7$ is —(CH$_2$)$_3$ and D is cis)

Refer to Chart A, step 3.

A solution of 25 mg of the less polar 9Z compound of Example 1, 235 mg of t-butyldimethylsilylchloride and 214 mg of imidazole in 5 ml of dimethylformamide is stirred in a nitrogen atmosphere for 24 hr at 50° C. The reaction mixture is then cooled to 0°, poured into 1:1 brine/water, and extracted with 1:1 ethyl acetate/hexane. The extracts are washed with water and brine, dried over anhydrous magnesium sulfate, and concentrated in vacuo. The crude product is chromatographed on a column containing 18 g of silica gel. The column is packed with 20% ethyl acetate/hexane and then eluted in 2-3 ml fractions with 60 ml of 30% and 100 ml of 40% ethyl acetate/hexane.

Fractions 48-46 are combined based on similar Rf values and yield 16 mg of pure title product as a viscous, colorless oil.

Using the procedure described above, 25 mg of the more polar 9-cis compound of Example 1 is converted to the title compound. The crude product is chromatographed on the column containing 15 g of silica gel packed with 20% ethyl acetate/hexane and eluted in 2-3 ml fractions with 50 ml of 30% and 100 ml of 40% ethyl acetate/hexane. Fractions 31-39 are combined based on similar Rf values and yield 22 mg of pure title product. This product is identical spectrally to the product prepared immediately above.

Alternatively, a solution of 1 mg of the product of Example 2 and 0.2 ml of acetone is cooled to 0° C. and treated with one drop of Jones Reagent. After 15 min at 0° C. 1 drop of isopropyl alcohol is added and the solvents are removed with a stream of nitrogen. The residue is partitioned between brine (1 ml) and ethyl acetate (0.2 ml). The product was 95% pure by TLC. Alternatively, solution of 1 mg of the compound of Example 2 and 0.2 ml of methylene chloride is treated at 25° C. with 0.2 ml of Collins Reagent (made up from 820 mg of chromium trioxide, 1.41 ml of pyridine and 5 ml of methylene chloride). After 15 min at 25° C., TLC analysis shows only the title product.

The titled product is also prepared by using the procedures and amounts identical to those of the previous paragraph, and employing the product of Example 4.

The titled product is characterized by IR absorptions observed at 1735, 1685, 1620, 1435, 1410, 1280, 1240, 1220, 1200, 1160, and 850 cm$^{-1}$. NMR absorptions (CDCl$_3$, $\delta$) are observed at $\delta$ 7.12-6.97 (M, 1H), 6.45-5.65 (M, 2H), 5.55-5.27 (M, 2H), 4.90-4.40 (M, 1H), 3,80-3.4 (S at 3.66 superimposed on M, 4H total) and 3.10-2.75 ppm (M, 2H).

EXAMPLE 11

(5Z,9Z)-8-(4,5-dihydro-5-isoxazolyl)-11-oxo-5,9-heptadecadienoic acid (Formula I, $X_1$ is —COOH, $Z_1$ is cis —CH=CH—(CH$_2$)$_3$—, $M_1$ is oxo, $R_3$ and $R_4$ are hydrogen, $R_7$ is —(CH$_2$)$_3$—CH$_3$ and D is cis)

A solution of 280 mg of the cis-11-hydroperoxides corresponding to the titled product in 1.025 g of t-butyldimethylsilylchloride and 925 mg of imidazole in 10 ml of dimethylformamide is heated at 50° C. under an atmosphere of nitrogen for 65 hr.

The reaction mixture is then cooled to room temperature and treated with 20 ml of 1:1 acetic acid/water (to hydrolyze the silyl ester). After 2 hrs at 25° C., the reaction mixture is poured into brine and extracted with 1:1 ethyl acetate/hexane. The extracts are washed five times with brine, dried over anhydrous magnesium sulfate and evaporated. The crude product is chromatographed on a 20 g column of silica gel. The column is packed with 15% acetone/hexane and eluted with 100 ml of 15% acetone/hexane containing 1% acetic acid. The column is then eluted with 200 ml of 25% acetone/hexane containing 1% acetic acid in 3 ml fractions. Fractions 26-42 are combined based on similar Rf values and yield 130 mg of the crude titled product. TLC analysis with 50% ethyl acetate/hexane containing 1% acetic acid shows 10-15% of a slightly less polar impurity. The partially purified product (130 mg) is rechromatographed on a column containing 85 g of 40-60$\mu$ silica gel. The column is equilibrated with 15% ethyl acetate/hexane containing 0.5% acetic acid and eluted in 5 ml fractions with 50% ethyl acetate/hexane containing 0.5% acetic acid. Fractions 60-68 are combined based on similar Rf values and yield 81 mg of pure titled product as a colorless oil which crystallizes on scratching. Trituration of a small sample with cold 15% ethyl acetate/hexane gives a colorless solid with a melting point of 62°-63° C.

IR absorptions are observed at 3100, 2650, 1700, 1690, 1615, 1410, 1280, 1230, and 850 cm$^{-1}$. NMR absorptions (CDCl$_3$, $\delta$) are observed at $\delta$ 9.75 (S, 1H, shifts downfield on cooling), 7.15-7.00 (M, 1H), 6.5-5.65 (M, 2H), 5.55-5.25 (M, 2H), 4.90-4.45 (M, 1H), 3.90-3.20 (M, 1H) and 3.10-2.75 ppm (M, 2H).

EXAMPLE 12

(5Z,9E)-8-(4,5-dihydro-5-isoxazolyl)-11-oxo-5,9-heptadecadienoic acid, methyl ester (Formula I, $X_1$ is —CO$_2$—CH$_3$, $Z_1$ is cis—CH=CH—(CH$_2$)$_3$—, $M_1$ is oxo, $R_3$ and $R_4$ are hydrogen, $R_7$ is —(CH$_2$)$_3$—CH$_3$ and D is trans)

Following the procedure of the preceding examples the titled compound is prepared from the corresponding 9E 11-hydroperoxide.

IR absorptions are observed at 1735, 1690, 1675, 1630, 1600, 1370, 985 and 845 cm$^{-1}$. NMR absorptions (CDCl$_3$, $\delta$) are observed at $\delta$ 7.15-7.00 (M, 1H), 6.75-5.95 (M, 2H), 5.60-5.20 (M, 2H), 4.90-4.40 (M, 1H), 3.66 (S, 3H) and 3.10-2.80 ppm (M, 2H).

EXAMPLE 13

(5Z,9E)-8-(4,5-dihydro-5-isoxazolyl)-11-oxo-5,9-heptadecadienoic acid (Formula I, $X_1$ is —COOH, $Z_1$ is cis—CH=CH—(CH$_2$)$_3$—, $M_1$ is oxo, $R_3$ and $R_4$ are hydrogen, $R_7$ is —(CH$_2$)$_3$—CH$_3$ and D is trans)

Using the procedure of Example 11, the 11-hydroperoxide corresponding to the 11-oxo titled compound is converted to the enone acid. The crude product is chromatographed on a column containing 20 g of Mallinkrot CC-4 acid-washed silica gel. The column is packed with 20% ethyl acetate/hexane and eluted with 50 ml of the same solvent. An additional 150 ml of 30% ethyl acetate/hexane and 150 ml of 40% ethyl acetate/hexane were also used. Fractions 60-82 are combined based on similar Rf values affording 90 mg of pure titled product as a viscous, colorless oil.

IR absorptions are observed at 3100, 2650, 1705, 1665, 1625, 1280, 1235, 980, and 845 cm$^{-1}$. NMR absorptions (CDCl$_3$, $\delta$) are observed at $\delta$ 9.85 (S, 1H, shifts downfield on cooling), 7.15-7.04 (M, 1H), 6.85-5.95 (M, 2H), 5.65-5.25 (M, 2H), 4.90-4.45 (M, 1H), and 3.25-2.70 ppm (M, 2H).

EXAMPLE 14

(8R,9Z,11ξ)-8-(4,5-dihydro-5-isoxazolyl)-11-hydroperoxy-9-heptadecenoic acid methyl ester (Formula I, $X_1$ is $-CO_2CH_3$, $Z_1$ is $-(CH_2)_3-(CH_2)_2-$, $M_1$ is α-OOH:β-H or α-H:β-OOH, $R_3$ and $R_4$ are hydrogen, $R_7$ is $-(CH_2)_3-CH_3$ and D is cis) and (8R,9E,11ξ)-8-(4,5-dihydro-5-isoxazolyl)-11-hydroperoxy-9-heptadecenoic acid methyl ester (Formula I, $X_1$ is $-CO_2CH_3$, $Z_1$ is $-(CH_2)_3-(CH_2)_2-$, $M_1$ is α-OOH:β-H or α-H:β-OOH, $R_3$ and $R_4$ are hydrogen, $R_7$ is $-(CH_2)_3-CH_3$ and D is trans)

A solution of 690 mg of (9α,11α,13E)-9,11-(epoxyimino)-prosta-13-enoic acid, methyl ester in 70 ml of ethyl acetate is allowed to stand at 25° in air for several weeks until the reaction was completed. (Alternatively, the solution is saturated with oxygen and warmed to 50° C. for 18 hr.) Following removal of the solvent in vacuo, the residue is chromatographed on a column containing 285 g of 40–60μ silica gel. The column was equilibrated with 4 l of 20% ethyl acetate/hexane, then eluted with 3 l of the same solvent, followed by 5 l of 30% ethyl acetate/hexane. Fractions were combined based on similar Rf values. Fractions 42–55 contained 160 mg of the 9-cis less polar C-11 epimer. Fractions 64–78 contained 152 mg of the 9-trans, less polar C-11 epimer. Fractions 103–117 contained 94 mg of the 9-cis, more polar C-11 epimer. Fractions 125–142 contained 77 mg of the 9-trans, more polar C-11 epimer.

For the 9Z, less polar C-11 epimer, IR absorptions are observed at 3400, 1735, 1600, 1280, 1200, 1170, and 850 $cm^{-1}$. NMR absorptions ($CDCl_3$, δ) are observed at δ 8.64 (broad S, 1H, shifts downfield on cooling) 7.15–7.03 (M, 1H), 5.70–5.30 (M, 2H), 4.80–4.20 (M, 2H), 3.67 (S, 3H) and 3.05–2.65 ppm (M, 2H).

For the 9E, less polar C-11 epimer, IR absorptions are observed at 3400, 1735, 1600, 1280, 1200, 1170, 980, and 850 $cm^{-1}$. NMR absorptions ($CDCl_3$, δ) are observed at δ 8.27 (broad S, 1H, shifts downfield on cooling), 7.15–6.97 (M, 1H), 6.65–6.30 (M, 2H), 4.80–4.00 (M, 2H), 3.67 (S, 3H), and 3.10–2.65 ppm (M, 2H).

For the more polar 9Z C-11 epimer, IR absorptions are observed at 3620, 3530, 3420, 1730, 1600, 1440, 1220, 1180, 1050, and 850 $cm^{-1}$. NMR absorptions ($CDCl_3$, δ) are observed at δ 9.07 (broad S, 1H, shifts downfield on cooling), 7.14–6.95 (M, 1H), 5.70–5.15 (M-2H), 4.80–4.25 (M, 2H), 3.65 (S, 3H) and 3.08–2.75 ppm (M, 2H).

For the more polar 9E C-11 epimer, IR absorptions are observed at 3600, 3520, 3420, 1730, 1600, 1440, 1220, 1175, 1040, 980 and 850 $cm^{-1}$. NMR absorptions ($CDCl_3$, δ) are observed at δ 7.13–6.96 (M, 1H), 5.60–5.30 (M, 2H), 4.80–4.05 (M, 2H), 3.65 (S, 3H) and 3.05–2.70 ppm (M, 2H).

EXAMPLE 15

(8R,9Z,11ξ)-8-(4,5-dihydro-5-isooxazolyl)-11-hydroperoxy-9-heptadecenoic acid (less polar C-11 epimer) (Formula I, $X_1$ is $-COOH$, $Z_1$ is $-(CH_2)_3-(CH_2)_2-$, $M_1$ is α-OOH:β-H or α-H:β-OOH, $R_3$ and $R_4$ are hydrogen, $R_7$ is $-(CH_2)_3-CH_3$ and D is cis)

Refer to Chart D.

A solution of 86 mg of the less polar C-11 epimer of the methyl ester corresponding to the titled acid in 0.86 ml of ethanol is treated with a suspension of 860 mg of plexaura homonalla derived esterase in 17.2 ml of water and the resulting mixture is stirred vigorously at 25° for 18 hrs. Acetone is added, and the reaction mixture is stirred for 30 min longer, and filtered through a pad of Celite ®. The filtrate is concentrated in vacuo and the residue is partitioned between brine containing 1 ml of potassium bisulfate and ethyl acetate. The organic layer is washed with brine, dried over anhydrous magnesium sulfate and evaporated. The crude product is chromatographed on the column containing 20 g of silica gel. The column is packed with 20% ethyl acetate/hexane and eluted with 40% ethyl acetate/hexane followed by 40% ethyl acetate/hexane containing 0.5% acetic acid. Fractions 57–66 afford 36 mg of the titled product as a viscous, colorless oil.

IR absorptions are observed at 3280, 2650, 1705, 1605, 1280 and 850 $cm^{-1}$. TLC (silica gel) yields the following: Rf 0.31 (40% ethyl acetate/hexane, containing 1% acetic acid).

EXAMPLE 16

(8R,9E,11ξ)-8-(4,5-dihydro-5-isoxazolyl)-11-hydroperoxy-9-heptadecenoic acid (less polar C-11 epimer) (Formula I, $X_1$ is $-COOH$, $Z_1$ is $-(CH_2)_3-(CH_2)_2-$, $M_1$ is α-OOH:β-H or α-H:β-OOH, $R_3$ and $R_4$ are hydrogen, $R_7$ is $-(CH_2)_3-CH_3$ and D is trans)

Following the procedure of Example 15, 126 mg of the more polar C-11 epimer of the methyl ester corresponding to the titled product is converted to the acid using 1.26 g of coral esterase in 1.26 ml of ethanol and 25 ml of water. The crude product is chromatographed on a 20 g column of silica gel. The column is packed with 20% ethyl acetate/hexane and eluted with 40% ethyl acetate/hexane followed by 40% ethyl acetate/hexane containing 0.5% acetic acid. Fractions 51–63 yielded 58 mg of pure acid. Trituraton of a small sample with 0.5 ml of 20% ethyl acetate/hexane, followed by filtration and drying yielded 3 mg of the title product as colorless crystals with melting point of 84°–85° C.

IR absorptions (7% $CHCl_3$ solution) are observed at 3520, 2670, 1705, 1600, 1280, 1230, 1210, 980, 855 and 730 $cm^{-1}$. TLC (silica gel) yields the following: Rf 0.26 (40% ethyl acetate/hexane containing 1% acetic acid).

EXAMPLE 17

(8R,9Z,11ξ)-8-(4,5-dihydro-5-isoxazolyl)-11-hydroperoxy-9-heptadecenoic acid (more polar C-11 epimer) (Formula I, $X_1$ is $-COOH$, $Z_1$ is $-(CH_2)_3-(CH_2)_2-$, $M_1$ is α-OOH:β-H or α-H:β-OOH, $R_3$ and $R_4$ are hydrogen, $R_7$ is $-(CH_2)_3-CH_3$ and D is cis)

Following the procedure of Example 15, 68 mg of the more polar C-11 epimer of the methyl ester corresponding to the titled product is hydrolyzed using 1.7 g of coral esterase in 1.7 ml of ethanol and 35 ml of water. The hydrolysis is allowed to proceed for 4 days with vigorous stirring in 25° C. The product is isolated as described in Example 15. The crude product is chromatographed on a column containing 20 g of silica gel. The column is packed with 30% ethyl acetate/hexane and eluted with 40% ethyl acetate/hexane, 100 ml of 40% ethyl acetate/hexane with 0.5% acetic acid and finally with 100 ml of 45% ethyl acetate/hexane containing 0.5% acetic acid. Fractions 73–90 are combind based on similar Rf values and yield 16 mg of pure titled product. The compound is triturated with 0.5 ml of cold 20% ethyl acetate/hexane, filtered and dried yielding 3 mg of the titled product as colorless crystal with a melting point of 108°–110° C.

IR absorptions (7% CHCl$_3$ solution) are observed at 3520, 2670, 1705, 1600, 1280, 1230, 1210, 950 (w) and 850 cm$^{-1}$. TLC (silica gel) yields the following: RF 0.19 (40% ethyl acetate/hexane containing 1% acetic acid).

EXAMPLE 18

(8R,9E,11ξ)-8-(4,5-Dihydro-5-isoxazolyl)-11-hydroperoxy-9-heptadecenoic acid (more polar C-11 epimer) (Formula I, $X_1$ is —CO$_2$CH$_3$, $Z_1$ is (CH$_2$)$_3$—(CH$_2$)$_2$, is α-OOH:β-H or α-H:β-OOH, $R_3$ and $R_4$ are hydrogen, $R_7$ is —(CH$_2$)$_3$—CH$_3$ and D is trans)

Following the procedure of Example 15 and using a two day reaction time, the more polar C-11 epimer of the methyl ester corresponding to the titled product (50 mg) is hydrolyzed using 500 mg of coral esterase in 0.5 ml of ethanol and 10 ml of water. The crude product is chromatographed on 20 g of Mallinckrodt CC-4 acid-washed silica gel. The column is packed with 25% ethyl acetate/hexane and eluted with 100 ml of 40% ethyl acetate/hexane and 100 ml of 45% ethyl acetate/hexane in 3 ml fractions. Fractions 25–37 are combined and yield 29 mg of pure titled acid. The IR sample is triturated with 0.5 ml of cold 20% ethyl acetate/hexane, filtered and dried (0.1 mm, 25°, 1 hr), thereby affording 3 mg of colorless crystals exhibiting m.p. 78°–79° C.

IR absorptions are observed at (7% CHCl$_3$ solution) 3520, 2670, 1705, 1600, 1430, 1410, 1380, 1280, 1220, 980 and 855 cm$^{-1}$. TLC (silica gel) yields the following: RF 0.17 (40% ethyl acetate/hexane containing 1% acetic acid).

EXAMPLE 19

(8R,9Z)-8-(4,5-dihydro-5-isoxazolyl)-11-oxo-9-heptadecenoic acid, methyl ester (Formula I, $X_1$ is —CO$_2$CH$_3$, $Z_1$ is —(CH$_2$)$_3$—(CH$_2$)$_2$—, $M_1$ is oxo, $R_3$ and $R_4$ are hydrogen, $R_7$ is —(CH$_2$)$_3$—CH$_3$ and D is cis)

Refer to Chart A, step 3.

A solution of 22 mg of the less polar hydroperoxide corresponding to the titled product, 235 mg of t-butyldimethylsilylchloride and 214 mg of imidazole in 5 ml of dimethylformamide is stirred at 35° C. for 40 hrs, then at 50° C. for 18 hrs. The reaction mixture is poured into brine and extracted with 1:1 ethyl acetate/hexane. The extracts are washed with brine and dried over anhydrous magnesium sulfate, and concentrated in vacuo. The crude product is chromatographed on a column containing 20 g of silica gel. The column is packed with 20% ethyl acetate and eluted with 40% ethyl acetate/hexane. Fractions 9–13 were combined based on similar Rf values affording 13 mg of pure titled product as a viscous, colorless oil. Using the procedure of the preceding paragraph, the more polar hydroperoxide compound corresponding to the titled product is converted to the ketone. The crude product is chromatographed on 20 g of silica gel and the column is packed with 20% ethyl acetate and eluted with 40% ethyl acetate/hexane. Fractions 6–11 yield 14 mg of pure titled product. This material is identical to that obtained in the first paragraph in terms of its spectral data.

EXAMPLE 20

(8R,9E)-8-(4,5-dihydro-5-isooxazolyl)-11-oxo-9-heptadecenoic acid, methyl ester (Formula I, $X_1$ is —CO$_2$CH$_3$, $Z_1$ is —(CH$_2$)$_3$—(CH$_2$)$_2$—, $M_1$ is oxo, $R_3$ and $R_4$ are hydrogen, $R_7$ is —(CH$_2$)$_3$—CH$_3$ and D is trans)

Following the procedure described in Example 19, the titled product is prepared from the corresponding hydroperoxide compound. The product is a viscous, colorless oil.

EXAMPLE 21

(5Z,8R,9Z,11ξ)-8-(4,5-Dihydro-5-isoxazolyl)-11-hydroperoxy-5,9-heptadecadienoic acid (less polar C-11 epimer) (Formula I, $X_1$ is —COOH, $Z_1$ is cis—CH=CH—(CH$_2$)$_3$—, $M_1$ is α-OOH:β-H or α-H:β-OOH, $R_3$ and $R_4$ are hydrogen, $R_7$ is —(CH$_2$)$_3$—CH$_3$, D is cis)

A solution containing 635 mg of the less polar methyl ester in 6.35 ml of ethanol is diluted with 130 ml of water and treated with 6.35 g of Plexaura homomalla-derived esterase powder. The resulting brown suspension is stirred vigorously at 25° for 24 hr. The reaction mixture is then diluted with 800 ml of acetone, stirred 30 min longer at 25°, and filtered through a pad of Celite on a sintered glass funnel. Following removal of the acetone at reduced pressure, the residue is partitioned between ethyl acetate and brine containing 0.5 ml of 2 M potassium bisulfate. The organic layer is washed with brine, dried over anhydrous magnesium sulfate and evaporated. The residue is chromatographed on a column containing 80 g of silica gel. The column is packed with 20% ethyl acetate/hexane (+0.5% acetic acid) and eluted in 15 ml fractions, with 40% ethyl acetate/hexane containing 0.5% acetic acid. Fractions 21–30 are combined based on similar Rf value and yields 360 mg of pure titled product. On trituration, this material crystallized; recrystallization of 200 mg from 3:1 ethyl acetate/hexane yielded 145 mg of a colorless solid, melting point 49°–51°. The product gives a strong positive test for peroxides (the ferrous thiocyanate spray), indicating that the C-11 hydroperoxide has survived the hydrolysis conditions.

Continued elution of the above chromatogram (fractions 31–39) afforded an additional 154 mg of 85–90% pure product.

IR peaks are observed at 3280, 3000, 2670, 1705, 1605, 855 and 790 cm$^{-1}$. In the NMR spectrum (CDCl$_3$, δ) the following pertinent absorptions are observed: 8.15 (broad s, 2H, shifts downfield on cooling), 7.13 (broad s, 1H), 5.80–5.30 (m, 4H), 4.90–4.25 (m, 2H), and 3.01–2.65 ppm (m, 2H). The mass spectrum shows the following: M$^+$ not observed; Ions present at m/e 350, 316, 291, 264, 165. TLC (silica gel) yields the following: Rf 0.37 (50% ethylacetate:50% hexane 1% acetic acid), Rf 0.44 (20% acetate 80% CH$_2$Cl$_2$ with 1% acetic acid).

EXAMPLE 22

(5Z,8R,9E,11ξ)-8-(4,5-Dihydro-5-isoxazolyl)-11-hydroperoxy-5,9-heptadecadienoic acid (less polar C-11 epimer) (Formula I, $X_1$ is —COOH, $Z_1$ is cis—CH=CH—$(CH_2)_3$—, $M_1$ is α-OOH:β-H or α-H:β-OOH, $R_3$ and $R_4$ are hydrogen, $R_7$ is —$(CH_2)_3$—$CH_3$, D is trans)

Enzymatic hydrolysis of the less polar methyl ester corresponding to the titled product is performed as in Example 21, using 1.69 g of the ester 16.9 g of coral enzyme powder, 16.9 ml of ethanol and 345 ml of water at 25° C. for 24 hrs. The crude product is chromatographed on a column containing 285 g of 40–60μ silica gel. The column is equilibrated with 20% ethyl acetate/hexane (0.5% acetic acid) and eluted with 40% ethyl acetate/hexane containing 0.5% acetic acid 250 ml is collected into a single flask and then 25 ml fractions are collected.

Fractions 49–70 are combined and afford 1.09 g of titled product as a viscous, colorless oil, which shows a strongly positive peroxide test.

Fractions 71–85 contain an additional 94 mg, contaminated by 5–10% or a more polar impurity.

IR absorptions are observed at 3290, 3000, 2670, 1705, 1605, 970 and 850 cm$^{-1}$. The NMR (CDCl$_3$, δ) peaks observed at 8.05 (broad s, 2H, shifts downfield on cooling), 7.20–7.00 (m, 1H), 6.85–6.25 (m, 4H), 4.95–4.10 (m, 2HO and 3.15–2.70 ppm (m, 2H). In the mass spectrum M+ is not observed. Ions are present at m/e 350, 335, 334, 316, 266, 223, 206, and 165. TLC (silica gel) yields the following: Rf 0.32 (50% ethylacetate; 50% hexane, with 1% acetic acid), Rf 0.43 (20% acetone:80% CH$_2$Cl$_2$ with 1% acetic acid).

EXAMPLE 23

(5Z,8R,9Z,11ξ)-8-(4,5-Dihydro-5-isoxazolyl)-11-hydroperoxy-5,9-heptadecadienoic acid (more polar C-11 epimer) (Formula I, $X_1$ is -COOH, $Z_1$ is cis—CH=CH—$(CH_2)_3$—, $M_1$ is α-OOH:β-H or α-H:β-OOH, $R_3$ and $R_4$ are hydrogen, $R_7$ is —$(CH_2)_3$—$CH_3$, D is cis)

Using the procedure of Example 21, the more polar C-11 epimer of the methyl ester corresponding to the titled produce (1.3 g) is hydrolyzed enzymatically using 13 g of coral enzyme powder, 13 ml of ethanol and 265 ml of water at 25° C. for 14 hr. The crude product is chromatographed on a column containing 285 g of 40–60μ silica gel. The column is eluted with 40% ethyl acetate/hexane containing 0.5% acetic acid. One 400 ml fraction is collected and then 25 ml fractions are collected. Fractions 84–86 contains 95 mg of about 90% pure titled product slightly contaminated by an unknown less polar impurity. Fractions 87–130 are completely pure by TLC and upon combination yield 689 mg of product as a viscous, colorless oil with a ositive ferrous thiocynate test.

IR absorptions are observed at 3280, 3000, 2670, 1705, 1605, 885 and 800 cm$^{-1}$. The NMR (CDCl$_3$, δ) peaks observed are 8.45 (s, 2H, shifts downfield on cooling), 7.20–7.05 (m, 1H), 5.80–5.15 (m, 4H), 4.85–4.40 (m, 2H) and 3.15–2.85 ppm (m, 2H). In the mass spectrum M+ is not observed. Ions are present at m/e 350, 335, 316, 291, 280, 279, 264, and 165. TLC (silica gel) yields the following: Rf 0.25 (50% ethylacetate:50% hexane with 1% acetic acid), Rf 0.39 (20% acetone:80% CH$_2$Cl$_2$ with 1% acetic acid).

EXAMPLE 24

(5Z,8R,9E,11ξ)-8-(4,5-Dihydro-5-isoxazolyl)-11-hydroperoxy-5,9-heptadecadienoic acid (more polar C-11 epimer) (Formula I, $X_1$ is —COOH, $Z_1$ is cis—CH=CH—$(CH_2)_3$—, $M_1$ is α-OOH:β-H or α-H:β-OOH, $R_3$ and $R_4$ are hydrogen, $R_7$ is —$(CH_2)_3$—$CH_3$, D is trans)

Following the procedure of Example 23, 1.1 gm of the more polar C-11 epimer of the ester corresponding to the titled product is enzymatically hydrolyzed with 11 gm of coral esterase powder, 11 ml of ethanol and 225 ml of water at 25° C. for 14 hrs. The crude product is chromatographed on a column containing 350 gm of silica gel. The column is packed with 25% ethyl acetate/hexane (with 0.5% acetic acid) and eluted with 40% ethyl acetate/hexane (with 0.5% acetic acid). One 400 ml fraction is collected and then 25 ml fractions are collected. Fractions 131-135 contain 40 mg of 90% pure titled product contaminated with an unknown less polar impurity.

Fractions 136–200 are homogeneous by TLC and are combined, affording 720 mg of pure acid product as a viscous, colorless oil which crystallized on trituration. Recrystallization from ether/hexane gives 280 mg with melting point 30°-32° C. The mother liquors, 375 mg are still completely pure by TLC, crystallizing spontaneously at 5° C.

IR absorptions are observed at 3280, 3000, 1705, 1605, 980 and 850 cm$^{-1}$. The NMR (CDCl$_3$, δ) peaks observed are 8.25 (broad s, 2H, shifts downfield on cooling), 7.20–7.05 (m, 1H), 6.70–6.35 (m, 4H), 4.85–4.05 (m, 2H) and 3.15–2.80 ppm (m, 2H).

In the mass spectrum M+ is not observed. Ions are present at m/e 350, 335, 334, 316, 264, 223, 206, and 165.

TLC (silica gel) yields the following: Rf 0.23 (50% ethylacetate:50% hexane with 1% acetic acid), Rf 0.39 (20% acetone:80% CH$_2$Cl$_2$ with 1% acetic acid).

EXAMPLE 25

Following the procedures of the preceding Examples isoxazolyl hydroperoxide compounds are prepared from biheterocyclic-9,11-trideoxy PGF-type compounds exhibiting the following side chain variations:
15-methyl-;
16-methyl-;
16,16-Dimethyl-;
16-Fluoro-;
16,16-Difluoro-;
17-Phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
16-Methyl-17-phenyl-18,19,20-trinor-;
16,16-Dimethyl-17-phenyl-18,19,20-trinor-;
16-Fluoro-17-phenyl-18,19,20-trinor-;
16,16-Difluoro-17-phenyl-18,19,20-trinor-;
16-Phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-Phenoxy-18,19,20-trinor-;
16-Methyl-16-phenoxy-18,19,20-trinor-;
13,14-Didehydro-;
16-Methyl-13,14-didehydro-;
16,16-Dimethyl-13,14-didehydro-;
16-Fluoro-13,14-didehydro-;

16,16-Difluoro-13,14-didehydro-;
17-Phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
16-Methyl-17-phenyl-18,19,20-trinor-13,14-didehydro-;
16,16-Dimethyl-17-phenyl-18,19,20-trinor-13,14-didehydro-;
16-Fluoro-17-phenyl-18,19,20-trinor-13,14-didehydro-;
16,16-Difluoro-17-phenyl-18,19,20-trinor-13,14-didehydro-;
16-Phenoxy-17,18,19,20-tetranor-13,14-didehydro-;
16-(m-trifluoromethylphenoxy)-17,18,19,20-tetranor-13,14-didehydro-;
16-(m-chlorophenoxy)-17,18,19,20-tetranor-13,14-didehydro-;
16-Phenoxy-18,19,20-trinor-13,14-didehydro-;
16-Methyl-16-phenoxy-18,19,20-trinor-13,14-didehydro-;
13,14-Dihydro-;
16-Methyl-13,14-dihydro-;
16,16-Dimethyl-13,14-dihydro-;
16-Fluoro-13,14-dihydro-;
16,16-Difluoro-13,14-dihydro-;
17-Phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trinor-13,14-dihydro-;
16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro-;
16-Methyl-16-phenoxy-18,19,20-trinor-13,14-dihydro-;

All of the compounds within the scope of this invention are prepared by these means.

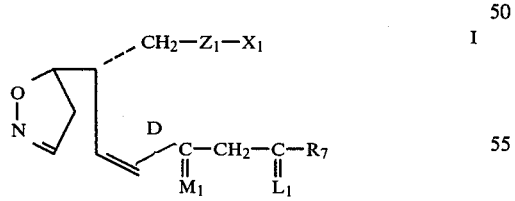

I

CHART A

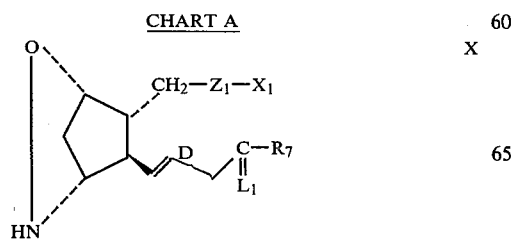

X

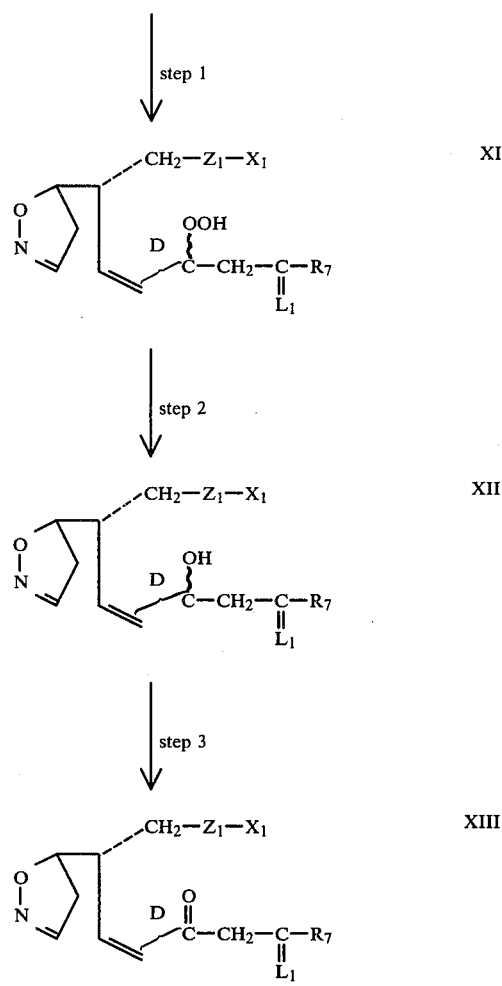

CHART B

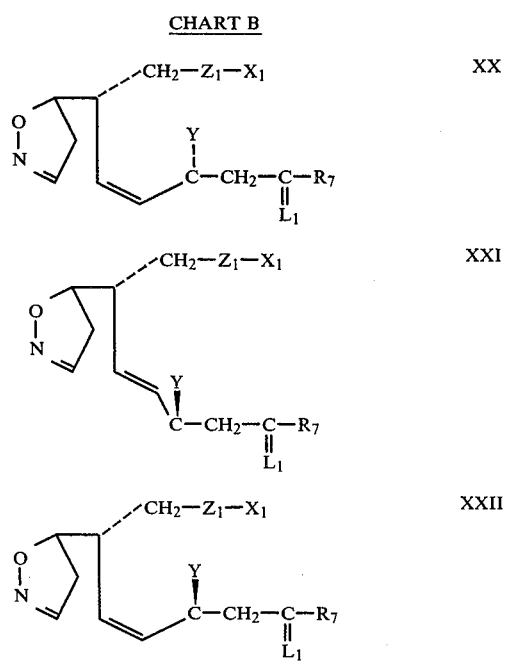

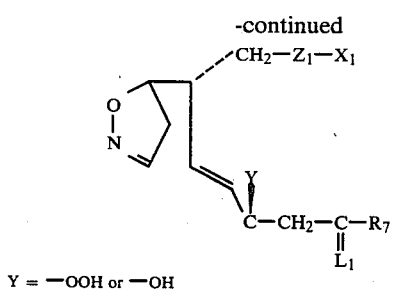

Y = —OOH or —OH

CHART C

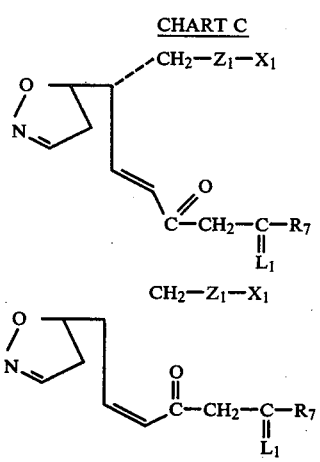

CHART D

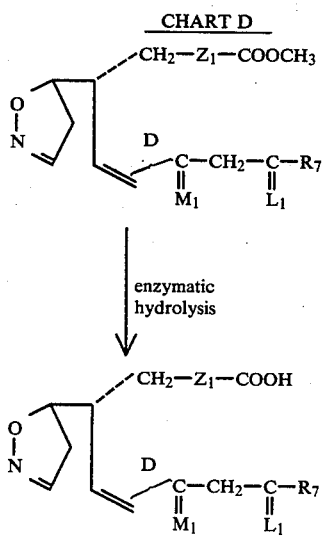

I claim:
1. A compound of the formula I

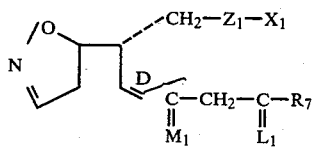

or a pharmacologically acceptable salt thereof, wherein D represents the E or Z configuration, wherein $M_1$ is oxo, $\alpha$-OH:$\beta$-H, $\beta$-OH:$\alpha$-H, $\alpha$-OOH:$\beta$-H, or $\beta$-OOH:$\alpha$-H;

wherein $X_1$ is (1) —$CO_2R_1$, wherein $R_1$ is hydrogen, alkyl of from one to 12 carbon atoms, cycloalkyl of from 3 to 10 carbon atoms, aralkyl of from 7 to 12 carbon atoms, phenyl, phenyl mono-, di-, or trisubstituted by chloro or alkyl of from one to 3 carbon atoms, or phenyl para-substituted by (i) —NHCO-$R_{25}$
(ii) —O—CO—$R_{26}$
(iii) —$CO_2R_1$
(iv) —C—CO—(p-Ph)—$R_{27}$
(v) —CH=N—NH—CO—$NH_2$ wherein $R_{25}$ is methyl, phenyl, acetamidophenyl, benzamidophenyl, or amino, $R_{26}$ is methyl, phenyl, amino or methoxy; $R_{27}$ is hydrogen or acetamido or a pharmacologically acceptable cation and —(p-Ph) is 1,4-phenylene, (2) —$COW_1$, wherein $W_1$ is
(a) amido of the formula —$NR_{21}R_{22}$, wherein $R_{21}$ and $R_{22}$ are hydrogen;
alkyl of one to 12 carbon atoms, inclusive;
cycloalkyl of 3 to 10 carbon atoms, inclusive;
aralkyl of 7 to 12 carbon atoms, inclusive;
phenyl;
phenyl substituted with one, 2, or 3 chloro, alkyl of one to 3 carbon atoms, inclusive, hydroxy, carboxy, alkoxycarbonyl of one to 4 carbon atoms, inclusive, or nitro;
carboxyalkyl of one to four carbon atoms, inclusive;
carbamoylalkyl of one to 4 carbon atoms, inclusive;
cyanoalkyl of one to 4 carbon atoms, inclusive;
acetylalkyl of one to 4 carbon atoms, inclusive;
benzoylalkyl of one to 4 carbon atoms, inclusive;
benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
pyridyl;
pyridyl substituted by one, 2, or 3 chloro, alkyl of one to 3 carbon atoms, inclusive, or alkoxy of one to 3 carbon atoms, inclusive;
pyridylalkyl of one to 4 carbon atoms, inclusive; or
pyridylalkyl substituted by one, 2, or 3 chloro, alkyl of one to 3 carbon atoms, inclusive, hydroxy, alkoxy of one to 3 carbon atoms, inclusive, hydroxyalkyl of one to 4 carbon atoms, inclusive, dihydroxyalkyl of one to 4 carbon atoms, inclusive, or trihydroxyalkyl of one to 4 carbon atoms inclusive;
with the further proviso that not more than one of $R_{21}$ and $R_{22}$ is other than hydrogen or alkyl;
(b) cycloamido selected from the group consisting of
1-pyrrolidinyl,
1-piperidinyl,
4-morpholinyl,
hexahydro-1H-azepin-1-yl, 3-pyrrolin-1-yl, or
3,6-dihydro-1(2H)-pyridinyl, substituted by $R_{21}$, or $R_{22}$ or both or
1-piperazinyl substituted on the 4-position by $R_{21}$, wherein $R_{21}$ and $R_{22}$ are as defined above;
(c) carbonylamido of the formula —$NR_{23}COR_{21}$, wherein $R_{23}$ is hydrogen or alkyl of one to 4 carbon atoms and $R_{21}$ is defined above;
(d) sulfonylamido of the formula —$NR_{23}SO_2R_{21}$, wherein $R_{21}$ and $R_{23}$ are as defined above; or (e) hydrazino of the formula—$NR_{23}R_{24}$, wherein $R_{24}$ is amido of the formula—$NR_{21}R_{22}$, as defined above, or cycloamido, as defined above; or (3) $CH_2OH$ (4) —$CH_2NR_{11}R_{12}$ wherein $R_{11}$ and $R_{12}$ are the same or different and are hydrogen or alkyl of from one to 4 carbon atoms; wherein $Z_1$ is (1) cis—CH=CH—$CH_2(CH_2)_g$—$CH_2$—,
(2) cis—CH=CH—$CH_2(CH_2)_g$—$CF_2$,
(3) cis—$CH_2$—CH=CH—$(CH_2)_g$—$CH_2$—,
(4) $CH_2)_3$—$(CH_2)_g$—$CH_2$
(5) —$(CH_2)_3$—$(CH_2)_g$—$CF_2$—,
(6) —$CH_2$—O—$CH_2$—$(CH_2)_g$—$CH_2$—,
(7) —(m-Ph)—$CH_2(CH_2)_g$—, or
(8) —(m-Ph)—O—$(CH_2)_g$—, wherein g is an integer from one to 3 and (m-Ph) is 1,3-phenylene;

wherein $L_1$ is $\alpha$-$R_3$:$\beta$-$R_4$, $\beta$-$R_3$:$\alpha$-$R_4$ or a mixture of the two, wherein $R_3$ and $R_4$ are the same or different and are hydrogen, methyl, of fluoro, with the proviso that if $R_3$ is fluoro, $R_4$ is hydrogen or fluoro;

wherein $R_7$ is (1) —$(CH_2)_m$—$CH_3$
(2) —O—(PhI) or
(3) —$(CH_2)_n$—(PhI)

wherein m is an integer from one to 5, n is an integer from 0 to 4, and (PhI) is phenyl substituted by from 0 to 3, chloro, fluoro, trifluoromethyl, alkyl of from one to 3 carbon atoms, or alkoxy of from one to 3 carbon atoms, with the proviso that not more than two substituents are other than alkyl.

2. A compound according to claim 1, wherein $X_1$ is —$COOR_1$.

3. A compound according to claim 2, wherein $Z_1$ is cis—CH=CH —$CH_2$—$(CH_2)_g$—$CF_2$—.

4. A compound according to claim 2, wherein $Z_1$ is cis—$CH_2$—CH=CH—$(CH_2)_g$—$CH_2$.

5. A compound according to claim 2, wherein $Z_1$ is —$(CH_2)_3$—$(CH_2)_g$—$CH_2$—.

6. A compound according to claim 2, wherein $Z_1$ is $(CH_2)_3$—$(CH_2)_g$—$CF_2$—.

7. A compound according to claim 2, wherein $Z_1$ is —$CH_2$—O—$CH_2$—$(CH_2)_g$—$CH_2$—.

8. A compound according to claim 2, wherein $Z_1$ is —(m-Ph)—$CH_2$—$(CH_2)_g$—.

9. A compound according to claim 2, wherein $Z_1$ is —(m-Ph)—O—$(CH_2)_g$—.

10. A compound according to claim 2, wherein $Z_1$ is cis—CH=CH—$CH_2$—$(CH_2)_g$—$CH_2$—.

11. A compound according to claim 10, wherein $R_7$ is —O—(PhI).

12. A compound according to claim 10, wherein $R_7$ is —$(CH_2)_m$—(PhI).

13. A compound according to claim 10, wherein $R_7$ is —$(CH_2)_m$—$CH_3$.

14. A compound according to claim 13, wherein g is 3.

15. A compound according to claim 13, wherein g is one.

16. A compound according to claim 15, wherein at least one of $R_3$ and $R_4$ is methyl.

17. A compound according to claim 16, wherein $R_3$ and $R_4$ are both methyl.

18. A compound according to claim 15, wherein at least one of $R_3$ and $R_4$ is fluoro.

19. A compound according to claim 18, wherein $R_3$ and $R_4$ are both fluoro.

20. A compound according to claim 15, wherein $R_3$ and $R_4$ are both hydrogen.

21. A compound of claim 1 wherein $X_1$ is —$CO_2H$ or —$CO_2$—$CH_3$, $Z_1$ is cis—CH=CH—$CH_2CH_2CH_2$—, $R_3$ and $R_4$ are hydrogen, and $R_7$ is —$(CH_3)_3CH_3$.

22. A compound of claim 21 wherein $M_1$ is oxo.

23. (5Z,9Z)-8-(4,5-dihydro-5-isoxazolyl)-11-oxo-5,9-heptadecadienoic acid, methyl ester, a compound of claim 22.

24. (5Z,9Z)-8-(4,5-dihydro-5-isoxazolyl)-11-oxo-5,9-heptadecadienoic acid, a compound of claim 22.

25. (5Z,9E)-8-(4,5-dihydro-5isoxozolyl)-11-oxo-5,9-heptadecadienoic acid, methyl ester, a compound of claim 22.

26. (5Z,9E)-8-(4,5-dihydro-5-isoxazolyl)-11-oxo-5,9-heptadecadienoic acid, a compound of claim 22.

27. A compound of claim 1, wherein $Z_1$ is —$(CH_2)_3$—$CH_2$.

28. (8R,9Z,11ξ)-8-(4,5-dihydro-5-isoxazolyl)-11-hydroperoxy-9-heptadecenoic acid, methyl ester, a compound of claim 27.

29. (8R,9E,11ξ)-8-(4,5-dihydro-5-isoxazolyl)-11-hydroperoxy-9-heptadecenoic acid, methyl ester, a compound of claim 28.

30. (8R,9Z,11ξ)-8-(4,5-dihydro-5-isoxzaolyl)-11-hydroperoxy-9-heptadecenoic acid, a compound of claim 29.

31. (8R,9E,11ξ)-8-(4,5-dihydro-5-isoxazolyl)-11-hydroperoxy-9-heptadecenoic acid, a compound of claim 29.

32. A compound of claim 29, wherein $M_1$ is oxo.

33. (8R,9Z)-8-(4,5-dihydro-5-isoxazolyl)-11-oxo-9-heptadecenoic acid, methyl ester, a compound of claim 32.

34. (8R,9E)-8-(4,5-dihydro-5-isoxazolyl)-11-oxo-9-heptadecenoic acid, methyl ester, a compound according to claim 32.

35. A compound of claim 1, wherein $Z_1$ is cis—CH=CH—$(CH_2)_3$—, $M_1$ is $\alpha$-OOH:$\beta$-H or $\alpha$-H:$\beta$-OOH, $R_3$ and $R_4$ are hydrogen, and $R_7$ is —$(CH_2)_3$—$CH_3$.

36. (5Z,8R,9Z,11ξ)-8-(4,5-dihydro-5-isoxazolyl)-11-hydroperoxy-5,9-heptadecadienoic acid, methyl ester, a compound of claim 35.

37. (5Z,8R,9E,11ξ)-8-(4,5-dihydro-5-isoxazolyl)-11-hydroperoxy-5,9-heptadecadienoic acid, methyl ester, a compound of claim 35.

38. A compound of claim 21, wherein $M_1$ is $\alpha$-OH:$\beta$-H or $\alpha$-H:$\beta$-OH.

39. (5Z,8R,9Z,11ξ)-8-(4,5-dihydro-5-isoxazolyl)-11-hydroxy-5,9-heptadecadienoic acid, methyl ester, a compound of claim 37.

40. (5Z,8R,9E,11ξ)-8-(4,5-dihydro-5-isoxazolyl)-11-hydroxy-5,9-heptadienoic acid, methyl ester, a compound of claim 37.

41. A compound of claim 37, wherein $X_1$ is $CO_2H$.

42. (5Z,8R,9Z,11ξ)-8-(4,5-dihydro-5-isoxazolyl)-11-hydroxy-5,9-heptadecadienoic acid, a compound of claim 41.

43. (5Z,8R,9E,11ξ)-8-(4,5-dihydro-isoxazolyl)-11-hydroxy-5,9-heptadecadienoic acid, a compound of claim 41.

44. (5Z,8R,9Z,11ξ)-8-(4,5-dihydro-5-isoxazolyl)-11-hydroperoxy-5,9-heptadecadienoic acid, a compound of claim 41.

45. (5Z,8R,9E,11ξ)-8-(4,5-dihydro-5-isoxazolyl)-11-hydroperoxy-5,9-heptadecadienoic acid, a compound of claim 41.

* * * * *

UNITED STATES PATENT OFFICE
CERTIFICATE OF CORRECTION

Patent No. 4,275,213    Dated   23 June 1981

Inventor(s)   Gordon L. Bundy

It is certified that error appears in the above-identified patent and that said Letters Patent are hereby corrected as shown below:

Column 6, line 16, "β-OH:β-H" should read -- α-OH:β-H --.
Column 9, line 54, "XIi" should read -- XII --.
Column 10, line 50, "(CHCL$_3$," should read -- (CDCl$_3$, --.
Column 19, line 16, "(CH$_2$)$_3$-(CH$_2$)$_2$, is" should read -- -(CH$_2$)$_3$-(CH$_2$)$_2$-, M is --.
Column 21, line 57, "a ositive" should read -- a positive --.
Column 23, line 55 should read as follows instead of as in the patent:

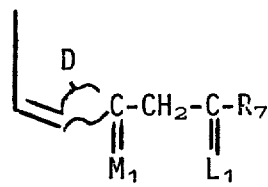

Column 23, line 65 should read as follows instead of as in the patent:

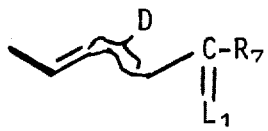

Column 24, line 14 should read as follows instead of as in the patent:

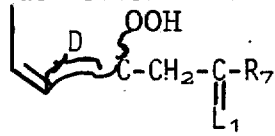

Column 24, line 26 should read as follows instead of as in the patent:

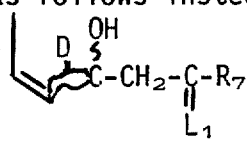

Column 24, line 38 should read as follows instead of as in the patent:

UNITED STATES PATENT AND TRADEMARK OFFICE
CERTIFICATE OF CORRECTION

PATENT NO. : 4,275,213
DATED : 23 June 1981
INVENTOR(S) : Gordon L. Bundy

It is certified that error appears in the above—identified patent and that said Letters Patent is hereby corrected as shown below:

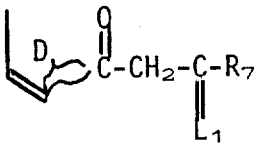

Column 24, line 59 should read as follows instead of as in the patent:

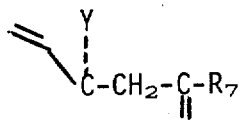

Column 25, line 25 should read as follows instead of as in the patent:

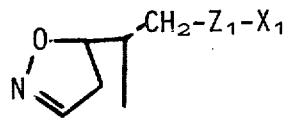

Column 25, line 39 should read as follows instead of as in the patent:

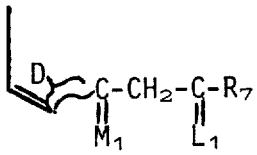

Column 25, line 52 should read as follows instead of as in the patent:

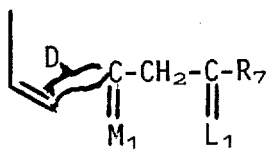

Column 25, line 61 should read as follows instead of as in the patent:

UNITED STATES PATENT AND TRADEMARK OFFICE
CERTIFICATE OF CORRECTION

PATENT NO. : 4,275,213

DATED : 23 June 1981

INVENTOR(S) : Gordon L. Bundy

It is certified that error appears in the above—identified patent and that said Letters Patent is hereby corrected as shown below:

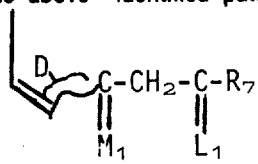

Column 27, line 11, "(4) $CH_2)_3-(CH_2)_g-CH_2$" should read -- $-(CH_2)_3-(CH_2)_g-CH_2-$ --.

Signed and Sealed this

Seventh Day of December 1982

[SEAL]

Attest:

GERALD J. MOSSINGHOFF

Attesting Officer

Commissioner of Patents and Trademarks